(12) United States Patent
Peter et al.

(10) Patent No.: US 8,871,748 B2
(45) Date of Patent: Oct. 28, 2014

(54) RETINAL CYCLODEXTRIN ACETALS AND HEMIACETALS FOR TREATING SKIN COMPLEXION DISORDER

(71) Applicant: Island Kinetics Inc., Chandler, AZ (US)

(72) Inventors: David Wayne Peter, San Tan Valley, AZ (US); John Dillon Stanek, Mesa, AZ (US); Cheria L Orozco, Scottsdale, AZ (US); Shyam K Gupta, Scottsdale, AZ (US)

(73) Assignee: Island Kinetics Inc., Chandler, AZ (US)

( * ) Notice: Subject to any disclaimer, the term of this patent is extended or adjusted under 35 U.S.C. 154(b) by 0 days.

(21) Appl. No.: 13/767,495

(22) Filed: Feb. 14, 2013

(65) Prior Publication Data

US 2013/0172291 A1   Jul. 4, 2013

Related U.S. Application Data

(63) Continuation-in-part of application No. 13/226,661, filed on Sep. 7, 2011, now Pat. No. 8,410,079.

(51) Int. Cl.
| | |
|---|---|
| *C08B 31/00* | (2006.01) |
| *A61Q 19/08* | (2006.01) |
| *A61Q 17/04* | (2006.01) |
| *A61K 45/06* | (2006.01) |
| *A61K 8/60* | (2006.01) |
| *A61Q 19/00* | (2006.01) |
| *A61K 8/73* | (2006.01) |
| *A61Q 5/00* | (2006.01) |
| *A61Q 19/02* | (2006.01) |
| *A61K 48/00* | (2006.01) |

(52) U.S. Cl.
CPC .............. *C08B 31/00* (2013.01); *A61Q 17/04* (2013.01); *A61K 45/06* (2013.01); *A61K 8/60* (2013.01); *A61Q 19/007* (2013.01); *A61Q 19/004* (2013.01); *A61K 8/738* (2013.01); *A61Q 19/00* (2013.01); *A61K 48/00* (2013.01); *A61Q 19/08* (2013.01); *A61Q 5/006* (2013.01); *A61Q 19/02* (2013.01); *A61Q 19/008* (2013.01)
USPC ........................................................ 514/100

(58) Field of Classification Search
USPC ........................................................ 514/100
See application file for complete search history.

(56) References Cited

U.S. PATENT DOCUMENTS 4,371,673 A * 2/1983 Pitha .............................. 525/426

* cited by examiner

*Primary Examiner* — Mina Haghighatian
*Assistant Examiner* — Luke Karpinski
(74) *Attorney, Agent, or Firm* — Arent Fox LLP

(57) ABSTRACT

The present invention discloses certain polyene cyclodextrin acetals and hemiacetals that are effective in providing skin clarification, which is useful for the treatment of acne, and skin disfigurements and skin darkening resulting from acne; skin darkening from cancer, diabetes, radiation treatments, chemotherapy, and sun-burn; mitochondrial and DNA dysfunction; age spots; loss of cellular antioxidants; skin changes associated with aging including collagen loss, loss of skin pliability, loss of skin suppleness, skin wrinkles and fine lines, oxidation, damage from radiation, damage from free radicals, and damage from UV; dry skin; xerosis; ichthyosis; dandruff; brownish spots; keratoses; melasma; lentigines; liver spots; skin pigmentation including pigmented spots, dark circles under the eyes, darkened skin, and blemishes; oily skin; warts; eczema; pruritic skin; psoriasis; inflammatory dermatoses; topical inflammation; disturbed keratinization; scalp dryness, and combinations thereof.

16 Claims, 3 Drawing Sheets

RETINAL CYCLODEXTRIN ACETALS AND HEMIACETALS FOR TREATING SKIN COMPLEXION DISORDER

The present invention is a continuation-in-part of U.S. patent application Ser. No. 13/226,661 (filed Sep. 7, 2011), which is incorporated herein by reference.

BACKGROUND OF THE INVENTION

The enhancement of physical appearance occupies greater focus in human life than nearly all other daily life-related actions. There are far more consumer products available for the beautification of human body than for the treatment of human ailments. The improvement of skin tone and appearance is a growing, multi-billion dollar industry encompassing cosmetic, nutraceutical, pharmaceutical, and physical therapy disciplines. The consumer attention is focused on newest miracle ingredient in age-defying, anti-wrinkle, skin smoothing, skin brightening, and other similar antiaging agents, the newest prior art examples of which follow.

Skin clarification has become an item of current marketing and consumer interest. Skin Clarifying products perform multiple functions via a single treatment scheme comprised of two to three products in a kit or set. This is a rapidly growing market representing age groups from teens to adults, even seniors. Skin clarifying market in USA is estimated at $2 billion, with over 20 million consumers of such products. Treatment benefits of such skin clarification agents include: (i) smoothing of skin damaged from acne scars, wounds' scars, markings left from diseases such as small pox, skin blemishes and skin "imperfections", (ii) balancing of skin tone from skin discoloration resulting from acne scars, wounds scars, markings left from diseases such as small pox, skin blemishes and other skin "imperfections", (iii) reduction or removal of age spots, skin spots, unpleasant "beauty marks", discoloration of stretch marks on abdomen from childbirth, and skin discoloration from exposure to sun, (iv) lightening of dark skin areas to brighten skin tone for better facial glow, (v) management of skin oiliness or skin dryness for clear complexion, (vi) turnover of dead skin cells to promote fresh growth for vibrant skin, (vii) reduction or removal of wrinkles and fine lines for smoother skin, and (viii) infusion of essential nutrients to promote healthy skin growth and glowing appearance.

The present invention provides a comprehensive scientific solution to the problems associated with the biology of skin that require skin clarification.

SUMMARY OF THE INVENTION

The present invention discloses certain polyene cyclodextrin hemiacetals and acetals of formula (Ia) and (Ib):

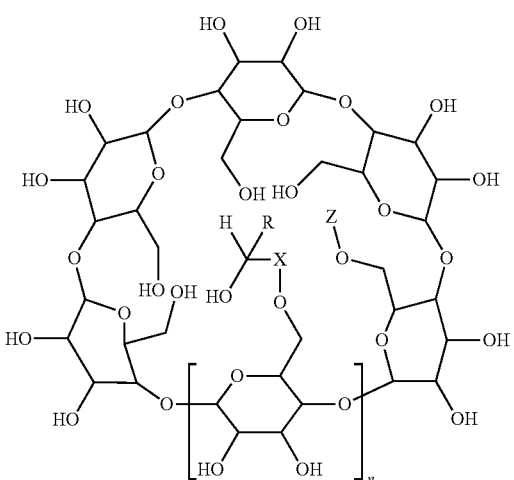

Polyene Cyclodextrin Hemiacetal

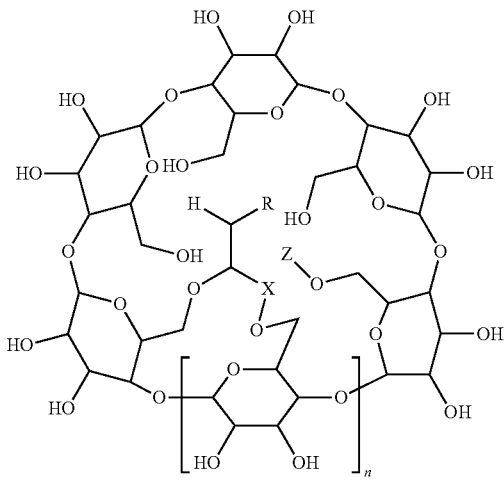

Polyene Cyclodextrin Acetal wherein,
n=0 to 4, and
X=a direct bond, —$CH_2$—$CH_2$—O—, or —$CH_2$—$CH_2$—$CH_2$—O—, and
Z=H, —$CH_2$—$CH_2$—OH, —$CH_2$—$CH_2$—$CH_2$—OH, —$SO_3$H,
—$SO_3$M, —$PO_3H_2$, —$PO_3$M, or —$PO_3M_2$, and
R=a retinoid, or a carotenoid, and
M=Na, K, Ca, Mg, Ba, Zn, Mn, Cu, Fe, Co, or Ni.

The compounds of formula (Ia) and (Ib) are effective in providing skin clarification, which is useful for the treatment of challenged skin from cancer, diabetes, radiation treatments, chemotherapy, and sun-burn; mitochondrial dysfunction; age spots; acne, loss of cellular antioxidants; skin changes associated with aging including collagen loss, loss of skin pliability, loss of skin suppleness, skin wrinkles and fine lines, oxidation, damage from radiation, damage from free radicals, and damage from UV; dry skin; xerosis; ichthyosis; dandruff; brownish spots; keratoses; melasma; lentigines; liver spots; skin pigmentation including pigmented spots, dark circles under the eyes, darkened skin, and blemishes; oily skin; warts; eczema; pruritic skin; psoriasis; inflammatory dermatoses; topical inflammation; disturbed keratinization; scalp dryness; skin depigmentation, and combinations thereof.

The following terms used herein have the meanings set forth below.

Challenged Skin. Skin ailments caused by the diseases of the internal organs and their treatments. Examples include challenged skin condition from diabetes, cancer, radiation treatments, chemotherapy, and sun-burn (solar radiation).

Chirally-Correct. A molecule, complex, or ion-pair having a tetrahedral carbon atom with three different substituents, said carbon atom being a chiral carbon atom, and said chirality limited to L (or S) configuration.

d or l; (+) or (−). These signify the direction of the optical rotation of a molecule.

Diastereomers. Diastereomers are stereoisomers that are not enantiomers.

Enantiomers. An enantiomer is one of two stereoisomers that are mirror images of each other that are non-superimposable.

Ion-Pair. A compound formed by ionic bond between an electron donor and an electron acceptor agent, or a positively charged and a negatively charged agent.

D or L; R or S. Dextro (D) and Levo (L); Rectus (R) or Sinister (S) relate to right- or left-handed configuration of a chiral molecule or atom, respectively. These terms do not signify the direction of optical rotation of said chiral molecule.

Organic. Being, containing, or relating to carbon compounds, especially in which hydrogen is attached to carbon whether derived from living organisms or non-living organisms.

Skin Clarification. Agents that provide treatment of certain dermatological disorders that include challenged skin from cancer, diabetes, radiation treatments, chemotherapy, and sun-burn; mitochondrial dysfunction; age spots; acne, loss of cellular antioxidants; skin changes associated with aging including collagen loss, loss of skin pliability, loss of skin suppleness, skin wrinkles and fine lines, oxidation, damage from radiation, damage from free radicals, and damage from UV; dry skin; xerosis; ichthyosis; dandruff; brownish spots; keratoses; melasma; lentigines; liver spots; skin pigmentation including pigmented spots, dark circles under the eyes, darkened skin, and blemishes; oily skin; warts; eczema; pruritic skin; psoriasis; inflammatory dermatoses; topical inflammation; disturbed keratinization; scalp dryness; skin depigmentation, and combinations thereof.

DESCRIPTION OF THE RELATED ART

Cyclodextrins are cyclic oligosaccharides which are composed of 6, 7 or 8 α(1-4)-linked anhydroglucose units. The α-, β- or γ-cyclodextrins (Drawings I, II, and III) prepared by the enzymatic conversion of starch differ in the diameter of their cavity and are generally suitable for inclusion or entrapment of a large number of organic substances, examples of which follow.

Cyclodextrins form inclusion complexes with many organic compounds, including pharmaceuticals [(Challa et al., AAPS Pharm Sci Tech, 6, E 329 (2005)].

Munoz et al. [(Journal of Pharmaceutical & Biomedical Analysis, 14, 909 (1996); Munoz et al., Analytica Chimica Acta, 227, 297 (1989)] disclose certain retinoid cyclodextrin complexes, including a retinal β-cyclodextrin complex.

Pitha (U.S. Pat. No. 4,371,673) discloses certain cyclodextrin complexes of retinoid polymers.

Moldenhauer et al. (U.S. Pat. No. 5,985,296) disclose a composition consisting of a complex selected from the group consisting of γ-cyclodextrin with retinal, and γ-cyclodextrin with a retinal derivative selected from the group consisting of retinyl esters and retinoic acid; wherein said retinal and retinal derivative and said γ-cyclodextrin are present in a weight ratio of retinol to γ-cyclodextrin ranging between 1:20 and 1:1.

Zawadzki et al. [(J Natl Cancer Inst. 65, 1011-5 (1985)] disclose a water-soluble, polymer-linked form of retinal. Retinal was conjugated to the hydrazide of carboxymethyl-dextran in the presence of alpha- and beta-cyclodextrins.

Loftsson et al. [(Pharmazie, 63, 171-9 (2008)] disclose that enhanced drug delivery through conjunctiva/sclera to retina can be obtained by formulating lipophilic drugs as hydrophilic drug/cyclodextrin complex solutions.

It is worthy of note that the above inclusion complexes of cyclodextrins, while they may have their own distinctive physical and chemical properties, are usually composed of two chemically different molecules (cyclodextrin being the host and another organic molecule being the guest) and there seems to be no covalent bond formation between the host and the guest molecules.

DETAILED DESCRIPTION

Figure 1:
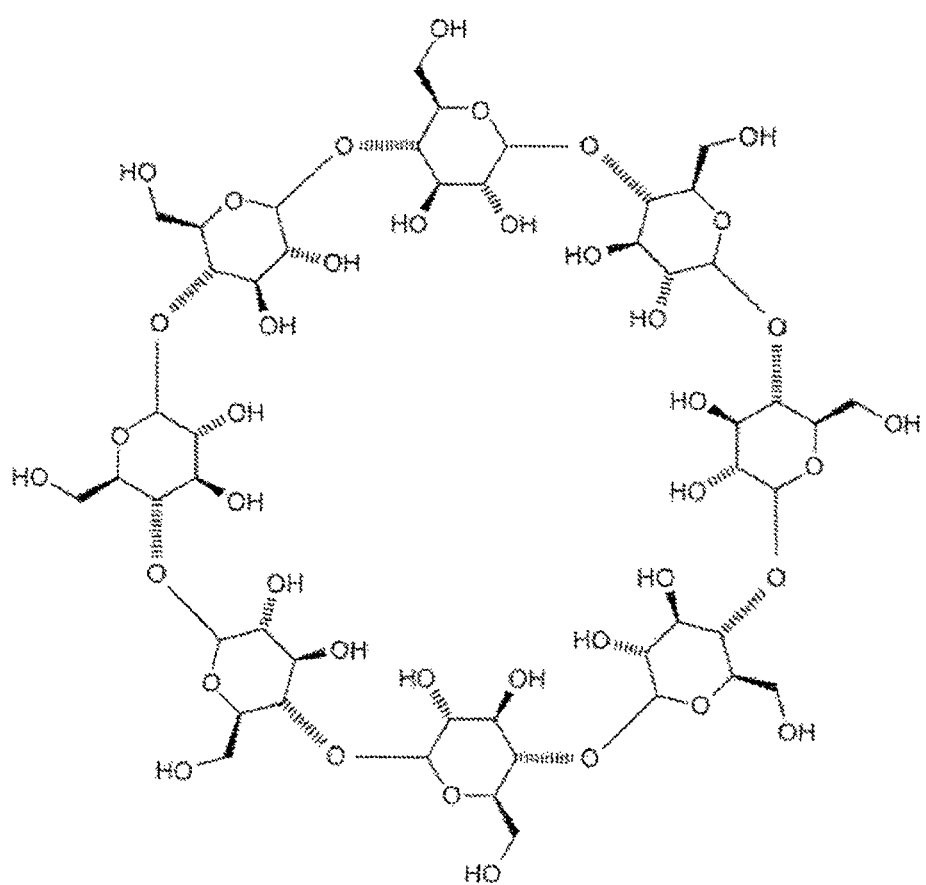
FIG. 1: γ-Cyclodextrin.
Figure 2:
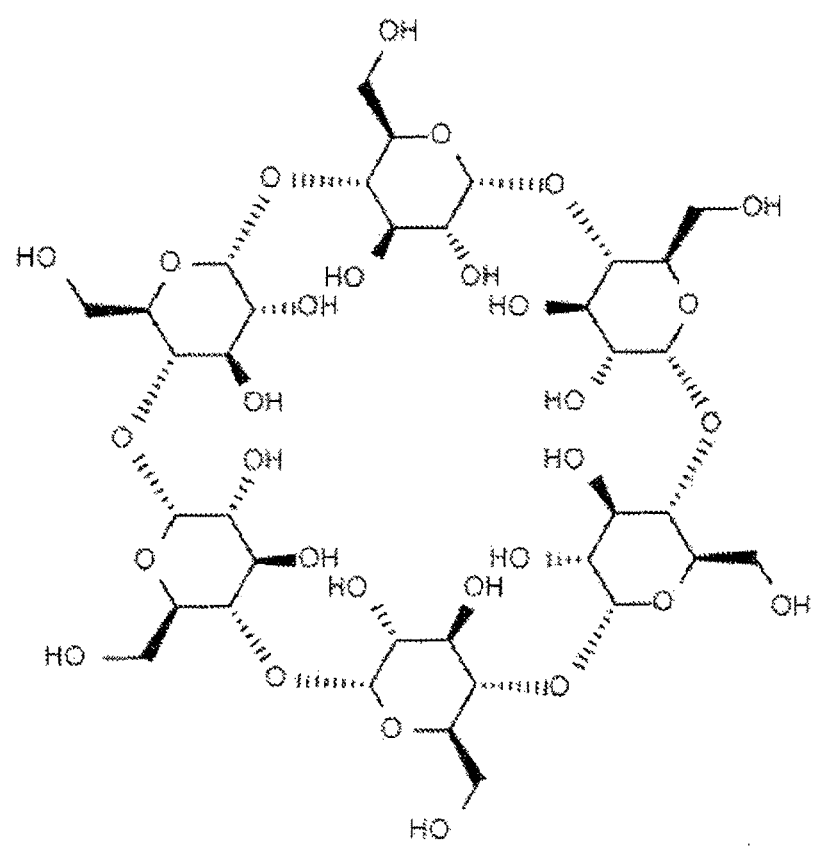
FIG. 2: α-Cyclodextrin.
Figure 3:
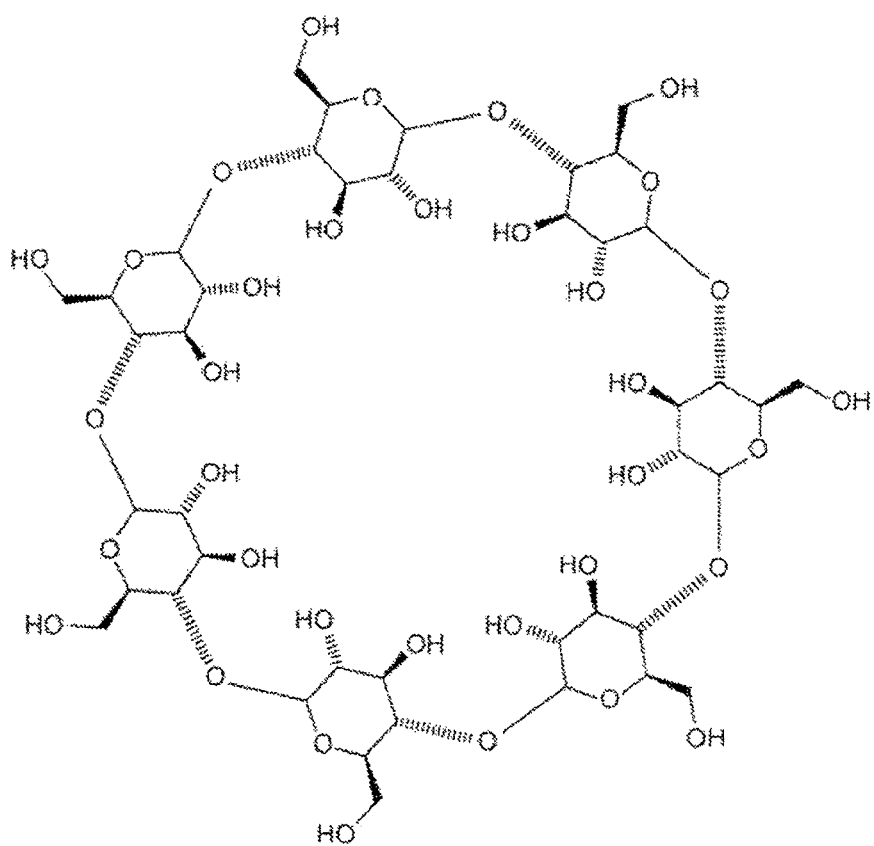
FIG. 3: β-Cyclodextrin.

The present invention discloses certain chirally correct retinal cyclodextrin acetals and hemiacetals of formula (Ia) and (Ib). These are prepared by the reaction of a polyene aldehyde, such as retinal, with a cyclodextrin, such as γ-cyclodextrin. There is a covalent chemical bond formation between said reacting molecules that results in the formation of the corresponding acetal or hemiacetal compounds. Additionally, the carbon atom at the hemiacetal or acetal position can have an (R) or (S) stereochemistry. These compounds can thus occur in their (R) or (S) stereoisomeric, racemic, or diastereomeric forms, as illustrated in formula (III) to (VI), all of which are useful for the biological skin treatment purpose of the present invention:

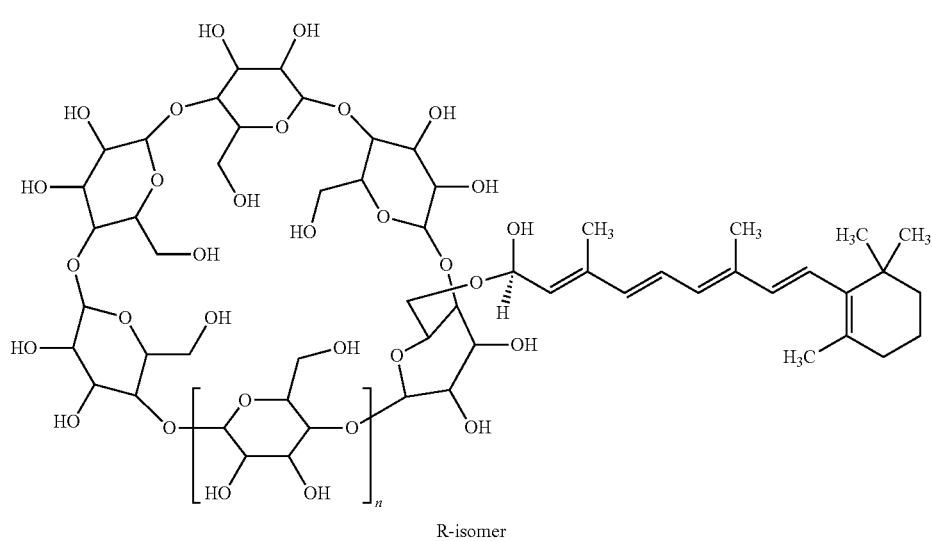

(V)

R-isomer

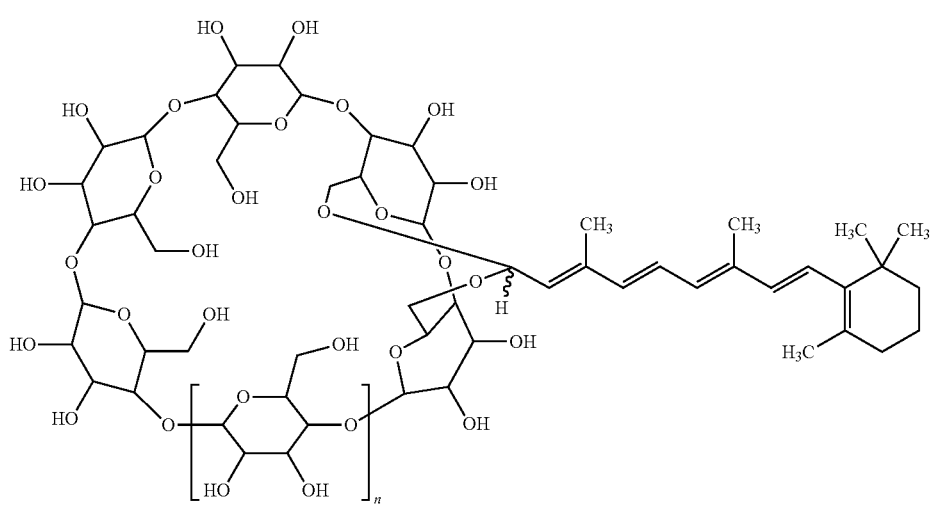
(VI)

wherein,
n=0 to 4.

The side-chain of the compounds of the present invention that is derived from a polyene aldehyde moiety can be oriented either the inside (endocyclic, formula VII) or the outside (exocyclic, formula VIII) of cyclodextrin moiety's polyhydroxylic cavity. This results in a plethora of stereochemical configurational and conformational structural possibilities.

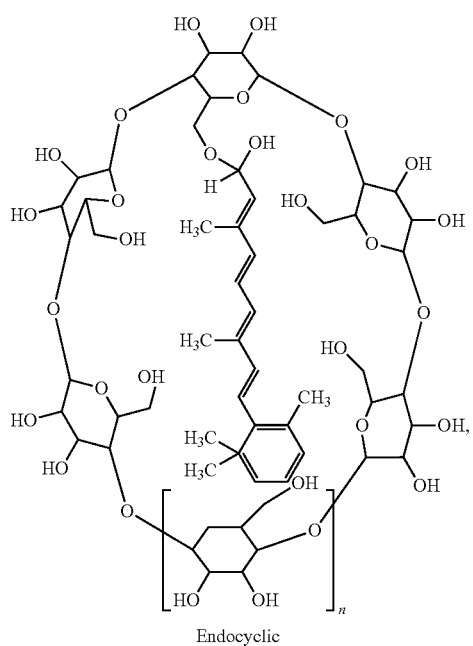

(VII)

Endocyclic

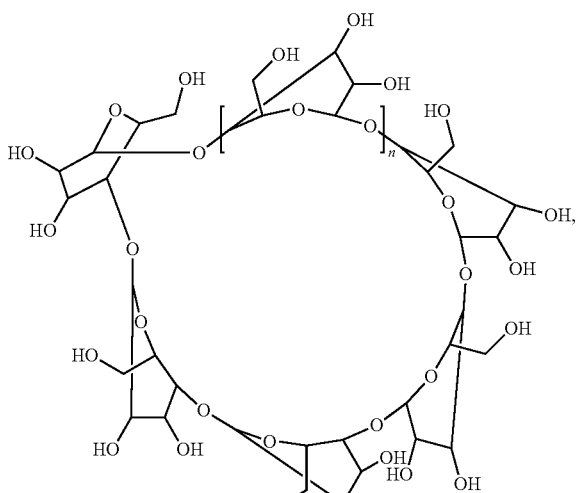

(VIII)

Exocyclic wherein,
n=0 to 4.

The compounds of the present invention are prepared by the process illustrated for compounds of formula (Ia and Ib) whereby a cyclodextrin (IX) is reacted with a polyenal (X), or a modification thereof;

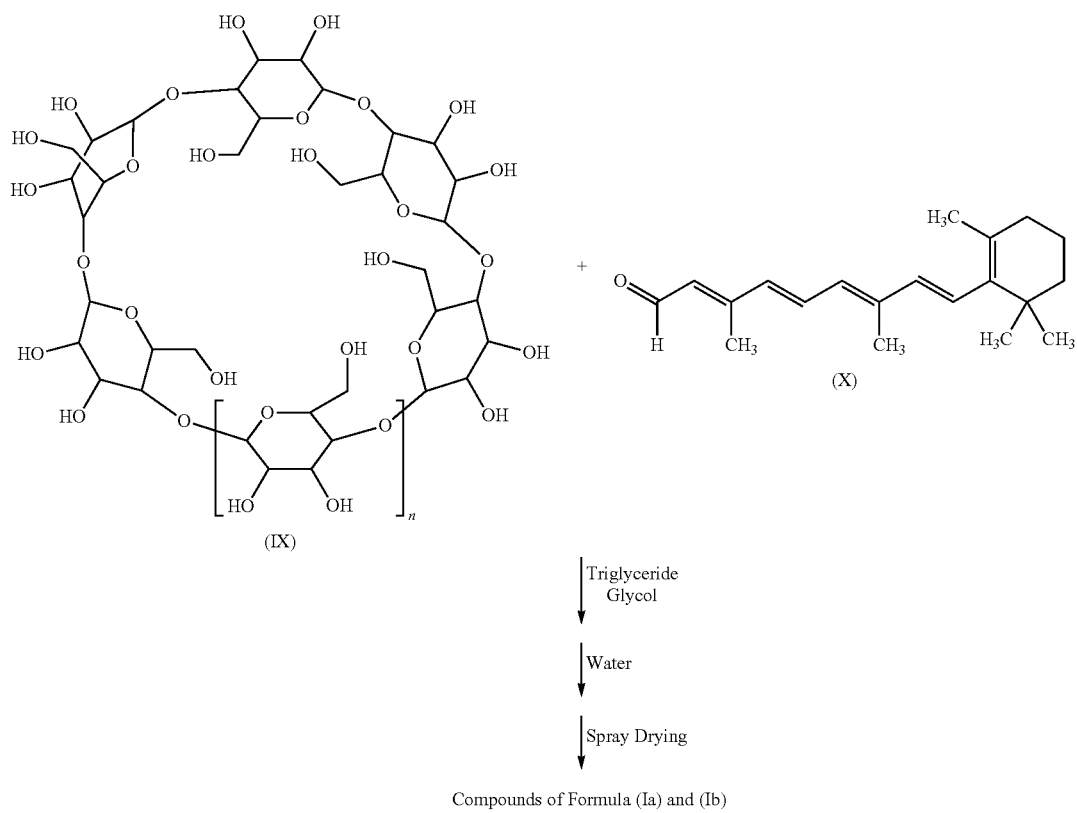

wherein, n=0 to 4.

The said process comprises (i) first mixing a polyene aldehyde, such as retinal, and an organic solubilizing liquid until a transparent mixture is obtained; (ii) to this mixture a suitable cyclodextrin and water are added and mixed for 1-120 hours under a nitrogen or argon atmosphere; (iii) the reaction mixture is then dried to a powder; (iv) the preferred method of drying is Pulse Combustion Spray Drying, which is a specialized spray drying technique designed to minimize exposure to any high temperature of product being dried. The organic solubilizing liquid is selected from the group comprising a triglyceride, a polyol, a fatty ester, or combinations thereof.

In the process of the present invention cyclodextrins and their derivatives, including hydroxyethyl- and hydroxypropyl cyclodextrins, sulfated cyclodextrins, phosphated cyclodextrins, and all forms of polyene aldehydes are useful.

In the process of present invention aldehydes other than retinal are also useful. In addition, isomers, analogs, and derivatives of retinal are also useful. Retinoid aldehydes and retinoid derivatives of retinal, including retinyl esters and other derivatives such as those disclosed by Ebrey et al (Biochemistry, 1975, 14 (18), pp 3933-3941), are also useful.

In the process of present invention a triglyceride, an alkyl or aryl ester of a C-10 to C-20 fatty acid, an alkyl or aryl ester of a C-10 to C-20 fatty alcohol, or a polyol and combinations thereof can be used as organic solubilizing liquids.

In the process of present invention an alkyl glycol, such as ethylene glycol, propylene glycol, glycerin, butylene glycol, pentylene glycol, hexylene glycol, methyl propanediol, polyethylene glycol, glycol ethers (such as ethoxydiglycol) can be used as organic solubilizing liquids.

In the process of present invention Pulse Combustion Spray Drying is used. Other methods of drying, such as fluidized bed drying, drum drying, solar drying, industrial spray drying, freeze drying, microwave drying, dielectric drying, impingement drying, pneumatic drying, flash drying, conveyor drying, can also be optimized for their use.

In the process of present invention a polyene aldehyde, such as a retinoid or a carotenoid aldehyde, is used, examples of which are of formula (XI) to (XV);

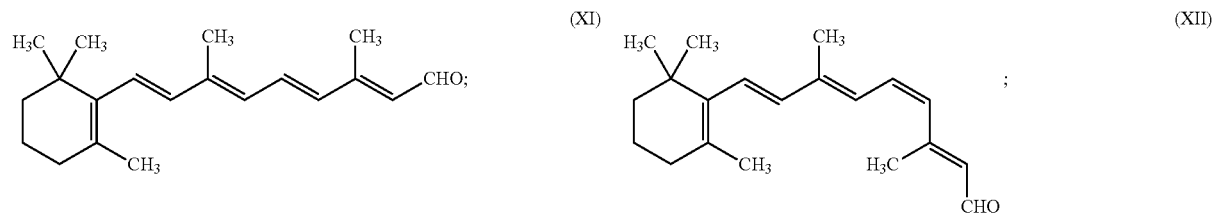

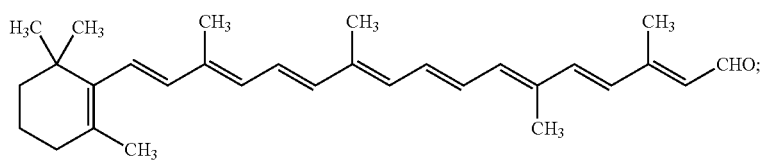
(XIII)

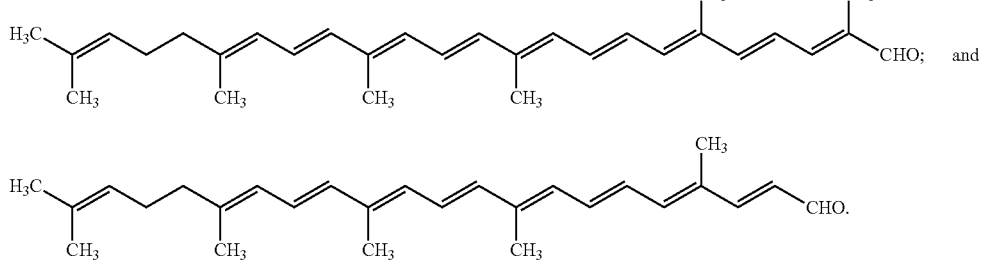
(XIV)

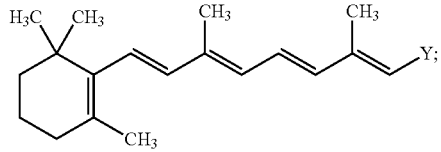
(XV)

This leads to a retinoid or a carotenoid side chain of the corresponding retinal or carotenal cyclodextrin hemiacetal or acetal, as in formula (XVI) to (XX);

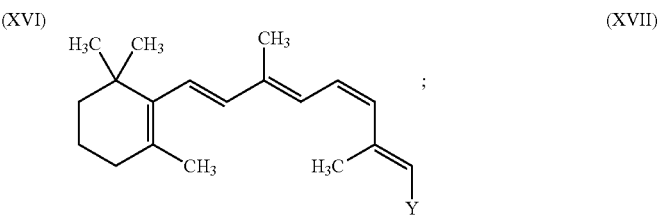
(XVI) (XVII)

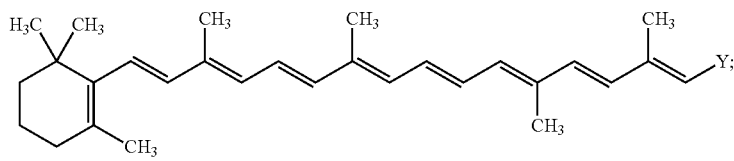
(XVIII)

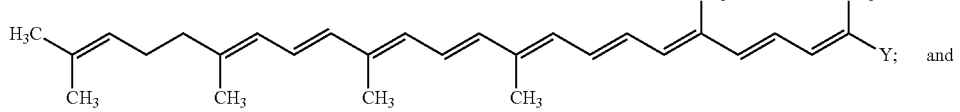
XIX)

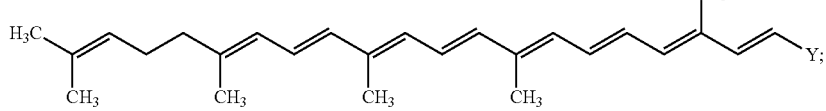
(XX)

wherein,
Y=point of attachment at hemiacetal or acetal carbon in formula (Ia) and (Ib).

The present invention also discloses a method to treat an ailment related to skin complexion from acne, and skin disfigurements and skin darkening resulting from acne; challenged skin from cancer, diabetes, radiation treatments, chemotherapy, and sun-burn; mitochondrial dysfunction; age spots; loss of cellular antioxidants; skin changes associated with aging including collagen loss, loss of skin pliability, loss of skin suppleness, skin wrinkles and fine lines, oxidation, damage from radiation, damage from free radicals, and damage from UV; dry skin; xerosis; ichthyosis; dandruff; brownish spots; keratoses; melasma; lentigines; liver spots; skin pigmentation including pigmented spots, dark circles under the eyes, darkened skin, and blemishes; oily skin; warts; eczema; pruritic skin; psoriasis; inflammatory dermatoses; topical inflammation; disturbed keratinization; scalp dryness, and combinations thereof; which comprises administering an effective amount of a composition comprising a compound of the present invention.

The compounds of the present invention possess the unique property of deacetalization when reacted with a low molecular weight straight chain alkanol, such as methanol. This reaction does not proceed with a branched chain alkanol, such as isopropanol, or a non-polar agent, such as chloroform. This deacetalization also occurs on topical application. The acidic pH of skin and the presence of topical moisture seem to be responsible for this reaction. This is illustrated below;

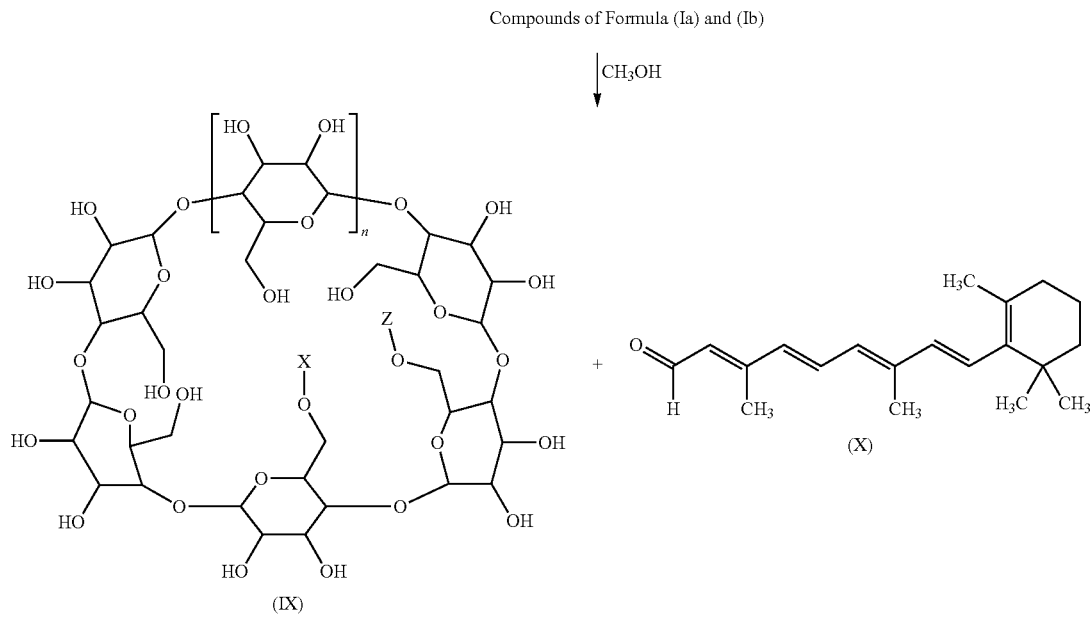

wherein,
n=0 to 4, and
X=H, and
Z=H, —CH$_2$—CH$_2$—OH, —CH$_2$—CH$_2$—CH$_2$—OH, —SO$_3$H,
—SO$_3$M, —PO$_3$H$_2$, —PO$_3$M, or —PO$_3$M$_2$, and
M=Na, K, Ca, Mg, Ba, Zn, Mn, Cu, Fe, Co, or Ni.

The compounds of the present invention treat certain dermatological disorders that include challenged skin from cancer, diabetes, radiation treatments, chemotherapy, and sunburn; mitochondrial dysfunction; age spots; acne, and skin disfigurements and skin darkening related to acne; loss of cellular antioxidants; skin changes associated with aging including collagen loss, loss of skin pliability, loss of skin suppleness, skin wrinkles and fine lines, oxidation, damage from radiation, damage from free radicals, and damage from UV; dry skin; xerosis; ichthyosis; dandruff; brownish spots; keratoses; melasma; lentigines; liver spots; skin pigmentation including pigmented spots, dark circles under the eyes, darkened skin, and blemishes; oily skin; warts; eczema; pruritic skin; psoriasis; inflammatory dermatoses; topical inflammation; disturbed keratinization; scalp dryness and combinations thereof.

It is preferred to have the compounds of the present invention incorporated in a suitable carrier base or a topical delivery system and any other desirable agents.

The role of antioxidants and free radical neutralizing agents in reducing skin aging process and skin wrinkle reduction is well known in the prior art. The antioxidants and free radical neutralizers can be included in the present invention for the protection of skin at the deeper skin renewal layers where fresh skin cells are generated. For this reason, an intracellular antioxidant or free radical neutralizer can also be beneficial. Among the antioxidants with multiple functions that are useful in combination with the agents of the present invention include Abyssine, Acai, Acetyl L-Cysteine, Acetyl L-Carnitine, L-Adenine, Adenosine, Aldavine, Aldenine, Alfalfa, Allantoin, Arbutin, Ambiaty, Ameliox, Arctic Cranberry, Arganyl, Artemisia, L-Ascorbic Acid, Ascorbyl Palmitate, Asiatic Acid, Astaxanthin, Beta Carotene, Betulinic Acid Extract, Bilberry, Blueberry Extract, Camu Camu, Canadian Willowherb, Catalase, Cat's Claw, Cherimoya, Cloudberry, Cranberry, Emblica, Gallic Acid, Giant Knotweed, Goji Berry, Green Tea Extract, Guava Extract, Heather Extract, Kakadu Plum, Kiwi Extract, Kudzu Zymbiozome *Fermentum*, Litchiderm, Lycopene, Magnesium Ascorbyl Phosphate, Magnolia Extract, Mangosteen, Marshmallow Extract, Melitane, Milk Thistle, MitoProtect (Nanoheart), Natrulon, Nectapure, Noni Extract, *Peumus Boldus* Leaf Extract, Phycocyanin, Phytic Acid, *Plantago, Pueraria Mirifica*, Pumpkin Extract, Quercetin, Red Clover, Red Wine Extract, Resveratrol, Retinyl Palmitate, *Rhodiola*, Rooibos Tea, Superoxide Dismutase, Tetrahydrocurcuminoids, Thioredoxin, Thioctic Acid, Thiotaine, Thyme Extract, Tocopherol, Tocopherol, Turmeric Extract, Ubiquinone, Venuceane, White Peony Extract, White Tea Extract, and combinations thereof.

Anti-inflammatory agents can be included in the present invention to reduce the skin irritation caused by environmental, personal hygiene, body beautification, and dietary/personal habits situations. Skin irritation is known to cause the degradation of collagen, which results in skin wrinkles. The examples of environmental conditions that can cause skin irritation include dry air, UV, sunlight, free radicals, air pollutants, and such. The examples of personal hygiene conditions that can cause skin irritation include use of soap and cleansers, shaving and hair removal agents, and such. The examples of body beautification that can cause skin irritation include fragrances, cosmetics, and other body decorative agents. The examples of dietary/personal habits conditions that can cause skin irritation include the use of foods rich in fats that can enhance prostaglandin synthesis in the body, excessive use of tobacco, and alcohol, all of which are known to cause skin irritation.

Most anti-inflammatory agents function by decreasing prostaglandin production through their inhibition of cyclooxygenase-1 (COX-1), cyclooxygenase-2 (COX-2), and lipoxygenase-5 (LOX-5) enzymes. The uses of massage or vasodilator ingredients for the removal of lactic acid from areas of inflammation are well known therapies. The initiation of inflammation by reactive oxygen species (such as superoxide anions) has been recognized. Recently, the role of Substance P in neurotransmission of pain from inflammatory response has been recognized. The inhibition of inflammatory cytokines in the development of new anti-inflammatory therapies is actively being studied. In addition, excessive nitric oxide (NO) production by activated macrophages has recently been implicated in several inflammatory diseases including arthritis. These aspects have been described in further detail in U.S. Pat. Nos. 5,494,668; 5,888,514; 5,854,291; and 5,916,565.

Collagen and fibrin boosting agents can also be included in the present invention. It is well known that with natural aging process the production of collagen and fibrin slows down. This causes skin thinning, loss of skin elasticity, and formation of wrinkles. The inclusion of collagen or fibrin boosting agents in any comprehensive antiaging treatment is thus of biological importance for skin regeneration.

It is well recognized in the scientific community that delivery systems are highly useful in cosmetics and pharmaceutical disciplines. In a recent article written by one of the present inventors (Cosmetic Delivery Systems, Household & Personal Products Industry, commonly known as HAPPI magazine, January 2003 issue, page 79) the definition and benefits of a number of prior art delivery systems have been discussed. A delivery system is thus a combination of both art and science that can improve the performance and consumer appeal of a consumer product or composition.

The present invention also discloses a topical delivery system comprising scientific combination of chirally correct mitoprotectant amino acid/ester and peptide complexes for healthy skin biology and a high-performance delivery system to provide a comprehensive solution to the problems associated with skin disorder. Said method of topical delivery for cellular energy support comprising mixing of, (i) a mitoprotectant compound of claim 1, and (ii) an antioxidant agent, and (iii) an anti-inflammatory agent, and (iv) a collagen-boosting agent with a carrier, and wherein said mixture is applied to skin.

Quaternary ammonium compounds have been commonly used in modern skin care agents for various benefits that include conditioning, shine, skin smoothing, and such. These ammonium compounds, which are cationic in nature, also contain an anionic counter-ion as an ion-pair. For example, Crodasorb UV-HPP (Polyquaternium-59) is a polymeric quaternary ammonium composition in which chloride and methosulfate are attached as anionic counter-ions. It is well appreciated by those who are versed in this art that only the cationic part of such quaternary ammonium agents provides skin care benefits such as preventing damage by UV, and protection of tensile strength, hydrophobicity, and protection of skin's natural color. In another example, Incroquat UV-283 (Cinnamidopropyltrimonium chloride), a UV-absorbing quaternary ammonium compound, provides protection from damage by UV and free radicals. In this example, the cationic Cinnamidopropyltrimonium moiety of this composition provides such benefits, and the anionic (chloride) part does not provide any skin beneficial effects. In the chirally correct mitoprotectant amino acid and peptide ion-pair complexes of the present invention both anionic and cationic moieties of said complexes provide cellular benefits to both dysfunctional mitochondria, and the folding of DNA.

The importance of intra-cellular antioxidants in antiaging agents has received spotlight in recent years. The incorporation of botanical antioxidants in cosmetic products is gaining popularity due to anti aging and other skin tone enhancement benefits, concordant to their use as nutritional supplements. Cosmetic products formulated with familiar antioxidants (vitamin E, Coenzyme Q10, ascorbic acid, lipoic acid, and soy isoflavones, etc.) have appeared in the marketplace with promissory claims. The design of a topical antioxidant product offers challenges: A wide spectrum antioxidant product should control intra-cellular oxidation resulting from biochemical mechanisms including oxygen, free radicals, UV, atmospheric pollutants, oxidative enzymes, catabolic oxidation, and chemical oxidation. The selection of functional intra-cellular antioxidants and free radical neutralizers to control complex, frequently inter-related biochemical oxidation mechanisms, and design of topical delivery systems to assure bioavailability via absorption through skin are of paramount importance.

A combination of antioxidants is more effective than a single antioxidant on an equal weight basis due to antioxidant cascade mechanism. It is well known that antioxidants belong to various chemical classes, such as polyphenols, carotenoids, flavonoids, and such. Some examples follow. (Chemical class is indicated in parentheses.) Rutin (flavone), Quercetin (flavone), Hesperidin (flavone), Diosmin (flavone), Mangiferin (xanthone), Mangostin (xanthone), Cyanidin (carotenoid), Astaxanthin (carotenoid), Xanthophyll (carotenoid), Lycopene (carotenoid), carotene (carotenoid), resveratrol, (polyphenol), tetrahydrocurcumin (polyphenol), rosmarinic acid (polyphenol), ellagic acid (polyphenol), hypericin (polyphenol), chlorogenic acid (polyphenol), oleuropein (polyphenol), lipoic acid (disulfide), glutathione-oxidized (disulfide), cystine (disulfide), N-acetyl-cystine (disulfide), glutathione-reduced (sulfhydryl), cystein (sulfhydryl), and N-acetyl-cysteine (sulfhydryl).

The present invention proposes that a combination of antioxidant ingredients should be included from different chemical classes to control intra-cellular oxidation resulting from various biochemical mechanisms. Most of these antioxidants also possess anti-inflammatory and antimicrobial properties. The total quantity of antioxidants should be balanced carefully, as an excessive amount of antioxidants may have an opposite, pro-oxidant effect resulting in poor stability and performance of the product. The use of antioxidant synergists offers additional advantages. The key function of such synergist is to reconvert the antioxidant free radical into its original non-radical state followed by its self-destruction into neutral, harmless molecules. Hydroxy acids (citric, ascorbic, tartaric, etc.), frequently used for this purpose. Coenzyme Q10, vitamin C, and quercetin have also been reported as synergists.

A great variety of collagen and fibrin boosting ingredients have now become commercially available that are also known to assist in the cellular functions. Such ingredients are also be included in the compositions of the present invention, the examples of which include *Withania Somnifera* Root Extract, *Ascophyllum Nodosum* Extract, *Asparagopsis Armata* Extract, *Veronica Appendiculata* Leaf Extract, *Betula Alba* (Birch) Bark/Leaf Extract, *Silybum Marianum* Fruit Extract, Aminoguanidine HCL, *Malus Domestica* Fruit Cell Culture, *Argania Spinosa* Leaf Extract, Acetyl Hexapeptide-8, *Vaccinium Myrtillus* (Bilberry) Extract, *Rubus Fructicosus* (Blackberry) Fruit Extract, *Borago Officinalis* Seed Oil, *Buddleja Davidii* Meristem Cell Culture, Tetrahexyldecyl Ascorbate, Carnosine (L), Catalase, *Centella Asiatica* Meristem Cell Culture, Caprooyl Tetrapeptide-3, Mixed Mucopolysacchardies, Glycogen, Tripeptide-2, *Leontopodium Alpinum* Meristem Cell Culture, *Phyllanthus Emblica* Fruit Extract, *Acmella Oleracea* Extract, *Vitex Agnus* Castus Extract, Ascorbyl Tetraisopalmitate, Palmitoyl Hexapeptide-6, *Lycium Barbarum* Extract (Goji Berry), *Macrocystis Pyrifera* Extract, *Saccharomyces/Xylinum* Black Tea Ferment, Pentapeptide-3, Soy Isoflavones, *Theobroma Cacao* (Cocoa) Seed Extract, *Camellia Sinensis* Leaf Extract, *Garcinia Mangostana* Peel Extract, *Litchi Chinesis* Pericarp Extract, *Machilus* Bark Extract, *Mallotus* Bark Extract, *Glycosaminoglycans, Citrus Aurantium Duclis* (Neroli) Flower Oil, sH-Polypeptide-15, *Simmondsia Chinensis* (Jojoba) Seed Oil, *Opuntia Ficus* Fruit Extract, *Pisum Sativum* (Pea Peptide) Extract, Acetyl Octapeptide-3, Dipeptide Diaminobutyroyl Benzylamide Diacetate, Palmitoyl Dipeptide-5, Palmitoyl Dipeptide-6, Thioctic (R-lipoic) Acid, L-Ergothioneine, Acetyl Tetrapetide-2, and Glycerin Soja (Soybean) Protein.

Anti-inflammatory agents are required in the present invention to reduce the skin irritation caused by environmental, personal hygiene, body beautification, and dietary/personal habits situations. It is to be noted that a mixture of two or more anti-inflammatory agents, especially those that belong to different biochemical mechanism classes, is more beneficial than corresponding equal weight amounts of a single ingredient. This is due to various different biochemical mechanisms by which such anti-inflammatory agents provide their beneficial effect. A number of both synthetic and natural agents have thus become available; some of such examples follow (the biochemical mechanisms of their action are indicated in the parentheses). Ginger Root, or *Zingiber Officinale* Root Extract (COX-2 inhibitor), *Galanga*, or *Alpinia Officinarum* Extract (LOX-5 inhibitor), Turmeric, or *Curcuma Longa* Root Extract (Superoxide inhibitor), Mango Ginger, or *Curcuma amada* (Unknown mechanism), tetuin, *Capsicum*, or *Capsicum Annuum* Extract (Substance P inhibitor, Vasodilation, Superoxide inhibitor), Clove Family, or *Syzygium Aromaticum* Extract (COX-1, COX-2 inhibitor), *Evodia*, or *Evodia Rutaecarpa* Fruit Extract, (COX-2 inhibitor), *Boswellia*, or *Boswellia Serrata* Extract (LOX-5 inhibitor), SAMe, or S-Adenosylmethionine (Catecholamine metabolism), *Eucomis*, or *Eucomis L"Herit* (COX-1 inhibitor), *Celastrus*, or *Celastrus orbiculatus* (COX-1 inhibitor), *Tithonia*, or *Tithonia diversifolia* (Cytokine inhibitor), *Kochia*, or *Kochia Scoparia* Extract (COX-2 inhibitor), *Scoparia*, or *Scoparia dulcis* Extract (Analgesic), Qiang Huo, or *Notopterygium incisum* (COX-1, LOX-5 inhibitor), Cinnamon, or *Cinnamonum cassia* (Nitric oxide scavenger), Mexican Bamboo, or *Polygonum cuspidatum* (Nitric Oxide scavenger), Ogon, Baikal Scullcap, or *Scutellaria baicalensis* (COX-2 inhibitor), *Coptis, Xianglian*, or *Coptis chinenesis* (Nitric oxide inhibitor), *Psoralea, Rumex, Baccharis*, Feverfew, *Vitis, Stephania* (unknown mechanisms), and *Corydalis*, or *Corydalis Turtschaninovii* Root Extract (Analgesic).

Ginger has been in use in Ayurvedic and Tibetan medicine for centuries. Ginger extracts are known to increase peripheral blood flow with a feeling of warming and tingling sensation. Ginger contains essential oils and spicy substances such as gingerol, shogaol, zingerone, and capsaicin; those spicy substances are principally responsible for its pain relieving properties. Recent scientific studies suggest that inhibiting the COX-2 enzyme may be an effective way to reduce inflammation without the side effects associated with irreversible COX-1 inhibition. Ginger inhibits COX-2, and also 5-lipoxygenase (LOX-5) enzyme.

Turmeric (*Curcuma longa*) rhizomes contain curcumin and its derivatives (curcuminoids) that are bright yellow in color. Their hydrogenated derivatives, tetrahydrocurcuminoids, are nearly colorless materials. All of these ingredients possess excellent anti-inflammatory activity. Tetrahydrocuminoids offer advantages in topical cosmetic applications due to their lack of color. The steam distillation of turmeric rhizomes provides turmeric oil, reported to possess excellent anti-inflammatory activity.

Galanga (*Alpinia officinarum*), also known as Galangal or Chinese Ginger, is native to China, Thailand, and India. It contains essential oils, gingerols, and a group of pungent substances, diarylheptanoids. The studies have shown diarylheptanoids (and analogous phenyl alkyl ketones) to possess excellent anti-arthritic properties due to their arrest of prostaglandin biosynthesis via inhibition of 5-lipoxygenase. *Capsicum*, Capsaicin: The ancient Maya folk-healers used cayenne pepper (*Capsicum frutescence*) for the treatment of toothache and general body pain. In modern Western medicine, capsaicin has been used to treat pain associated with neuralgia, neuropathy, osteoarthritis, rheumatoid arthritis, bladder pain, and stomach pain. Capsaicin is the active analgesic ingredient present in *capsicum* preparations. It is a topical analgesic that may inhibit the synthesis, transport, and release of substance P, a neurotransmitter of pain. Capsaicin is also a vasodilator.

Clove Family. Clove oil and clove buds have been in use for the treatment of toothache and muscular pains since ancient times. A number of plants in this family, notably *Syzygium aromaticum, Syzygium corynocarpum*, and *Syzygium mallacense*, are known to contain pain-relieving constituents. Eugenol, a vasorelaxant and analgesic constituent of *Syzygium aromaticum*, also possesses strong anti-inflammatory activity. The extracts of *Syzygium corynocarpum* and *Syzygium malaccense* inhibit prostaglandin biosynthesis via blocking of COX-1 and COX-2 enzymes. The extract from the bark of *Syzygium cumini* has been shown to possess excellent anti-inflammatory activity without any gastric side effects. Acetyl eugenol, a component of clove oil, has recently been shown to alter arachidonic acid metabolism, resulting in reduced formation of thromboxane.

*Evodia*: This herb has been used for dysentery in Chinese medicine (Wu Zhu Yu) since ancient times. Rutaecarpine, obtained from *Evodia rutaecarpa*, is a new class of recently introduced anti-inflammatory ingredients that directly inhibits COX-2 enzyme. Antinociceptive and anti-inflammatory activities of the extracts of this plant have recently been reported. Evodiamine, and its analogs present in *Evodia rutaecarpa* also possess vasodilatory and analgesic activity.

Frankincense, *Boswellia*: Guggal (*Boswellia serrata*) has been used for the treatment of arthritis in Ayurvedic medicine for centuries. Frankincense, myrrh, and gold were among three presents brought by the Wise Men to the infant Christ. It is interesting that all three of these have been used in the treatment of gout and arthritis in ancient history of medicine. *Boswellia* is currently one of the most popular alternative medicines for inflammation. Recent research has identified three key ingredients (grouped as boswellic acids) that are responsible for the anti-inflammatory action of *Boswellia serrata* extracts. Recent research has firmly established that Boswellic acids and their derivatives are specific inhibitors of leukotriene synthesis by their direct interaction with 5-lipoxygenase.

SAMe (S-Adenosylmethionine): It has received wide interest for the treatment of osteoarthritis since its discovery in 1952. This substance, present in all living organisms, is required for over 40 biochemical functions in human body. It has been proven to enhance the formation of cartilage, and provide pain relieving anti-inflammatory action.

*Eucomis*: South African traditional medicine has extensively utilized the extracts of bulb, leaves, and root of this plant for pain, inflammation, and fever. Recent work has shown that the extracts from bulb have the highest level of COX-1 inhibitory activity.

*Celastrus*: This oriental folk medicine has been used for rheumatoid arthritis. Recent work has identified strong COX-1 activity ascribed to epiafzelechin, a member of flavan-3-ols, present in this herb. *Tithonia*: The extracts of *Tithonia* are used in Central America for the treatment of haematomas. Recent work has shown the constituents of this extract, diversifolin and tirotundin, to possess anti-inflammatory activity. Interestingly, the anti-inflammatory activity was from the inhibition of the synthesis of inflammatory mediators such as cytokines and chemokines.

*Scoparia*: The herb *Scoparia dulcis* is used in Brazilian folk medicine to treat bronchitis, gastric disorders, hemorrhoids, insect bites and skin wounds, and in oriental medicine to treat hypertension. Recent studies have shown that extracts of *Scoparia dulcis* have analgesic, anti-inflammatory, and sympathomimetic activity.

Qiang Huo: The root extracts of this Chinese medicinal herb traditionally used for arthritis and joint pain have recently been shown to possess COX-1 and LOX-5 inhibitory activity.

Cinnamon: The traditional use of cinnamon as a vasodilator for pain and inflammation in the Middle Eastern and other countries has long been practiced. Recent disclosures have confirmed the anti-nociceptive and anti-inflammatory activity of cinnamon extract via its direct scavenging of nitric oxide and peroxynitrite.

*Polygonum*: This herb is more commonly known as Mexican Bamboo (Mexico) and Hu Zhang (China). Various species of *Polygonum* have recently been identified to contain anti-inflammatory constituents that modulate the production of NO by activated macrophages. Recent results suggest that *Polygonum tinctorium* extract may be a potential therapeutic modulator of NO synthesis in various pathological conditions.

Ogon (Ougon): *Scutellaria*, used in Japanese Kampo herbal medicine (Ogon), China, (Sanhuang), and in Baikal region of Russia, has shown anti-inflammatory, anti-hepatitis, antibacterial, antiviral, anti-tumor, and anti-oxidant activity. The anti-inflammatory activity is ascribed to its active components, baicalin, baicalein and wogonin. In a recent study, wogonin tested as a direct inhibitor of COX-2, NO-production, and prostaglandin production, indicating its potential use in the treatment of topical inflammatory diseases. Baicalin, in another study, showed chemokine inhibiting activity. Baikalein has shown LOX-5 inhibiting activity.

*Coptis*: *Coptis*, a Chinese herbal medicine (Xianglian) also used in Japan, is well known for its antibacterial properties due to its high berberine content. It also contains several lignans (isolariciresinol, lariciresinol glycoside, pinoresinol, pinoresinol glycoside, and syringaresinol glycoside) with anti-inflammatory properties. Woorenosides, isolated from *Coptis japonica*, have shown anti-inflammatory activity via their inhibition of NO production.

*Psoralea glandulosa*: An ancient Persian medicine, *Psoralea glandulosa* contains bakuchiol, cyclobakuchiols, and angelicin that possess anti-pyretic and anti-inflammatory activity. *Psoralea corylifolia*, an Ayurvedic medicine in India (Babchi) and BuGuZhi in China, possesses anti-inflammatory, anti-pyretic, and analgesic activity due to its bavachinin content. Bakuchiol, recently isolated from the same plant, inhibits NO synthase gene, with implications for its anti-inflammatory activity.

*Rumex patientia* (Dock) has shown anti-inflammatory activity.

*Baccharis*: Several species of *Baccharis* have shown analgesic and anti-inflammatory activity, principally due their inhibition of prostaglandin biosynthesis.

*Feverfew*: This phytopharmaceutical (*Tanacetum parthenium*) is well known for its fever and migraine alleviation benefits. Recently, its anti-nociceptive and anti-inflammatory activities, due to its LOX-5 and COX inhibition, have been reported *Vitis*: The grape family is well known for its potent antioxidant constituents, especially procyanidins and resveratrol. Recently, tetramers of resveratrol found in *Vitis amurensis*, have been found to possess strong anti-inflammatory activity via their inhibition of leukotriene biosynthesis. This is not surprising, as several antioxidants are also known to possess anti-inflammatory activity: This property may be due to their inhibitory effect on LOX and COX enzymes.

*Stephania*: *Stephania* has long been used in Korea as an analgesic and anti-inflammatory agent for joint swelling. Tetrandrine, an alkaloid found in *Stephania japonica* is well known for its anti-inflammatory activity. Cepharanthine, an alkaloid found in *Stephania cepharantha*, has revealed vasodilatory effects with enhanced microcirculation.

*Tinospora*: Ayurvedic and Islamic practitioners in India have used *Tinospora cardifolia* for liver jaundice, various skin diseases, rheumatism, fever, and syphilis. Clinical studies conducted with human arthritis have demonstrated its anti-inflammatory properties. The inhibition of nitric oxide synthesis appears to be a factor for this activity.

Additional examples of anti-inflammatory agents include Horse Chestnut Extract (*Aesculus hippocastanum* extract)), Esculin, Escin, Yohimbine, *Capsicum Oleoresin*, Capsaicin, Niacin, Niacin Esters, Methyl Nicotinate, Benzyl Nicotinate, Ruscogenins (Butchers Broom extract; *Ruscus aculeatus* extract), Diosgenin (*Trigonella foenumgraecum*, Fenugreek), Emblica extract (*Phyllanthus emblica* extract), Asiaticoside (*Centella asiatica* extract), Boswellia Extract (*Boswellia serrata*), Ginger Root Extract (*Zingiber Officianalis*), Piperine, Vitamin K, Melilot (*Melilotus officinalis* extract), Glycyrrhetinic acid, Ursolic acid, Sericoside (*Terminalia sericea* extract), Darutoside (*Siegesbeckia orientalis* extract), Amni visnaga extract, extract of Red Vine (*Vitis-Vinifera*) leaves, apigenin, phytosan, and luteolin.

Collagen and fibrin boosting agents are also required in the present invention. It is well known that with natural aging process the production of collagen and fibrin slows down. This causes skin thinning, loss of skin elasticity, and formation of wrinkles. The inclusion of collagen or fibrin boosting agents is thus of biological importance for skin regeneration. The collagen or fibrin boosting composition can be selected from, but not limited to, glucosamine, N-acetyl-glucosamine, chondroitin, algae extracts, chitosan, niacinamide, niacinamide derivatives, copper nucleotides, zinc nucleotides, manganese nucleotides, glutathione, carnosine, vitamin C, vitamin E, vitamin A, Coenzyme Q10, lipoic acid, dimethylamino ethanol, Ascorbic acid, Ascorbic acid derivatives, Glucosamine ascorbate, Arginine ascorbate, Lysine ascorbate, Glutathione ascorbate, Nicotinamide ascorbate, Niacin ascorbate, Allantoin ascorbate, Creatine ascorbate, Creatinine ascorbate, Chondroitin ascorbate, Chitosan ascorbate, DNA Ascorbate, Carnosine ascorbate, Vitamin E, various Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), Lipoic acid, Niacinamide lipoate, Glutathione, Andrographolide (*Andrographis paniculata*), Carnosine, Niacinamide, *Potentilla erecta* extract, Polyphenols, Grapeseed extract, Pycnogenol (Pine Bark extract), copper nucleotide, zinc nucleotide, manganese nucleotide, copper glucoside, zinc glucoside, manganese glucoside, and combinations thereof.

Since living parts of hair and nail are also very similar to skin in aging process, the agents of the present invention are also useful for hair and nail antiaging agents.

EXAMPLES

The following examples are presented to illustrate presently preferred practice thereof. As illustrations they are not intended to limit the scope of the invention. All quantities are in weight %.

Example 1

Preparation of Retinal γ-Cyclodextrin Hemiacetal

| Water | (Q.S. to) 100 |
|---|---|
| γ-Cyclodextrin | 37.00 |
| Retinal | 1.90 |
| Argania Spinosa (Argan) Nut Oil | 3.25 |
| Pentylene Glycol | 2.47 |

Procedure. This composition is prepared by first mixing the retinal, *Argania Spinosa* (Argan) Nut Oil and pentylene glycol until a transparent mixture is obtained. To this mixture γ-cyclodextrin and water are added and mixed for 1-120 hours under a nitrogen or argon atmosphere. The solution is then dried to a powder. The preferred method of drying is spray drying. The resulting powder after drying contains 5% to 15% water.

Example 2

Preparation of Retinal γ-Cyclodextrin Hemiacetal

| Water | (Q.S. to) 100 |
|---|---|
| γ-Cyclodextrin | 37.00 |
| Retinal | 1.90 |
| Pentylene Glycol | 5.72 |

Procedure. This composition is prepared by first mixing the retinal and pentylene glycol until a transparent mixture is obtained. To this mixture γ-cyclodextrin and water are added and mixed for 1-120 hours under a nitrogen or argon atmosphere. The solution is then dried to a powder. The solution is then dried to a powder. The preferred method of drying is spray drying. The resulting powder after drying contains 5% to 15% water.

Example 3

Preparation of Retinal γ-Cyclodextrin Acetal

| Water | (Q.S. to) 100 |
|---|---|
| γ-Cyclodextrin | 40.00 |
| Retinal | 2.20 |
| *Rubus chamaemorus* (seed) oil | 3.50 |
| Pentylene Glycol | 2.13 |
| *Lonicera Caprifolium* (Honeysuckle) Flower Extract (and) *Lonicera Japonica* (Honeysuckle) Flower Extract | 0.25 |

Procedure. This composition is prepared by first mixing the retinal, *Rubus chamaemorus* (seed) oil and pentylene glycol until a transparent mixture is obtained. To this mixture the .gamma, -cyclodextrin, water and *Lonicera Caprifolium* (Honeysuckle) Flower Extract (and) *Lonicera Japonica* (Honeysuckle) Flower Extract are added and mixed for 1-120 hours under a nitrogen or argon atmosphere. The solution is then dried to a powder. The solution is then dried to a powder. The solution is then dried to a powder. The preferred method of drying is spray drying. The resulting powder after drying contains 5% to 15% water.

Example 4

Preparation of Retinal γ-Cyclodextrin Hemiacetal

| Water | (Q.S. to) 100 |
|---|---|
| γ-Cyclodextrin | 42.00 |
| Retinal | 2.30 |
| *Simmondsia Chinensis* (Jojoba) Seed Oil | 3.70 |
| Pentylene Glycol | 2.33 |
| *Lonicera Caprifolium* (Honeysuckle) Flower Extract (and) *Lonicera Japonica* (Honeysuckle) Flower Extract | 0.25 |

Process. This composition is prepared by first mixing the retinal, *Simmondsia Chinensis* (Jojoba) Seed Oil and pentylene glycol until a transparent mixture is obtained. To this mixture the .gamma, -cyclodextrin, water and *Lonicera Caprifolium* (Honeysuckle) Flower Extract (and) *Lonicera Japonica* (Honeysuckle) Flower Extract are added and mixed for 1-120 hours under a nitrogen or argon atmosphere. The solution is then dried to a powder. The preferred method of drying is "Pulse Combustion Spray drying," a specialized Spray drying technique designed to minimized temperature of product being dried.

Example 5

Preparation of Body Emulsion

| Water | (Q.S. to) 100 |
|---|---|
| Glyceryl Monostearate | 4.00 |
| Stearic Acid | 2.20 |
| Cetyl Alcohol | 3.50 |
| Isopropyl Palmitate | 5.00 |
| Methyl Paraben | 0.20 |
| Powder made in Example 1 from above | 7.00 |

Process. Water, Glyceryl Monostearate, Stearic Acid, Cetyl Alcohol and Isopropyl Palmitate are heated to 65 C. This mixture is then homogenized using an Ultra Turax or a Fluidizer or other such homogenizer and cooled to below 30

C. To this the powder from Example 1 above is added and mixed along with the Methyl Paraben.

Example 6

Preparation of Body Emulsion

| Water | (Q.S. to) 100 |
|---|---|
| Glyceryl Monostearate | 4.00 |
| Stearic Acid | 2.20 |
| Cetyl Alcohol | 3.50 |
| Isopropyl Palmitate | 5.00 |
| Methyl Paraben | 0.20 |
| Powder made in Example 2 from above | 5.00 |

Process. Water, Glyceryl Monostearate, Stearic Acid, Cetyl Alcohol and Isopropyl Palmitate are heated to 65 C. This mixture is then homogenized using an Ultra Turax or a Fluidizer or other such homogenizer and cooled to below 30 C. To this the powder from Example 2 above is added and mixed along with the Methyl Paraben.

Example 7

Preparation of Body Emulsion

| Water | (Q.S. to) 100 |
|---|---|
| Glyceryl Monostearate | 4.00 |
| Stearic Acid | 2.20 |
| Cetyl Alcohol | 3.50 |
| Isopropyl Palmitate | 5.00 |
| Methyl Paraben | 0.20 |
| Powder made in Example 3 from above | 2.00 |

Process. Water, Glyceryl Monostearate, Stearic Acid, Cetyl Alcohol and Isopropyl Palmitate are heated to 65 C. This mixture is then homogenized using an Ultra Turax or a Fluidizer or other such homogenizer and cooled to below 30 C. To this the powder from Example 3 above is added and mixed along with the Methyl Paraben.

Example 8

Preparation of Sun Protection Composition

| Water | (Q.S. to) 100 |
|---|---|
| Emulsifying Wax NF | 6.00 |
| Ensulizole | 4.00 |
| Octinoxate | 4.00 |
| Propylene Glycol | 3.00 |
| Gluconolactone/Sodium Benzoate | 1.00 |
| Triethanolamine | 0.35 |
| Ammonium Acryloyldimethyltaurate/VP Copolymer | 1.40 |
| Titanium Dioxide | 0.75 |
| Powder made in Example 1 | 7.00 |

Process. Water, Emulsifying Wax NF, Ensulizole, Octinoxate and Propylene Glycol are heated to 80 C and mixed. This mixture is then cooled to below 30 C. While continue to mix the following are added; Gluconolactone/Sodium Benzoate, Triethanolamine and Titanium Dioxide. To this the powder from Example 1 above is added.

Example 9

Preparation of Sun Protection Factor (SPF) Product

| Water | (Q.S. to) 100 |
|---|---|
| Emulsifying Wax NF | 6.00 |
| Ensulizole | 4.00 |
| Octinoxate | 4.00 |
| Propylene Glycol | 3.00 |
| Gluconolactone/Sodium Benzoate | 1.00 |
| Triethanolamine | 0.35 |
| Ammonium Acryloyldimethyltaurate/VP Copolymer | 1.40 |
| Titanium Dioxide | 0.75 |
| Powder made in Example 2 | 4.00 |

Process. The water, Emulsifying Wax NF, Ensulizole, Octinoxate and Propylene Glycol are heated to 80 C and mixed. This mixture is then cooled to below 30 C. While continue to mix the following are added; Gluconolactone/Sodium Benzoate, Triethanolamine and Titanium Dioxide. To this the powder from Example 2 above is added.

Example 10

Preparation of Sun Protection Factor (SPF) Product

| Water | (Q.S. to) 100 |
|---|---|
| Emulsifying Wax NF | 6.00 |
| Ensulizole | 4.00 |
| Octinoxate | 4.00 |
| Propylene Glycol | 3.00 |
| Gluconolactone/Sodium Benzoate | 1.00 |
| Triethanolamine | 0.35 |
| Ammonium Acryloyldimethyltaurate/VP Copolymer | 1.40 |
| Titanium Dioxide | 0.75 |
| Powder made in Example 3 | 2.00 |

Process. The water, Emulsifying Wax NF, Ensulizole, Octinoxate and Propylene Glycol are heated to 80 C and mixed. This mixture is then cooled to below 30 C. While continue to mix the following are added; Gluconolactone/Sodium Benzoate, Triethanolamine and Titanium Dioxide. To this the powder from Example 3 above is added.

Example 11

Anti-Wrinkle Cream

| Water | (Q.S. to) 100 |
|---|---|
| Hydroxypropyl Starch Phosphate | 2.00 |
| Candelilla/Jojoba/Rice Bran Polyglyceryl-3 Esters (and) Glyceryl Stearate (and) Cetearyl Alcohol (and) Sodium Stearoyl Lactylate | 7.00 |
| Polyglyceryl-10 Pentastearate (and) Behenyl Alcohol (and) Sodium Stearoyl Lactylate | 2.00 |
| Glycerin | 5.50 |
| Cetyl Alcohol | 0.80 |
| Stearyl Alcohol | 0.80 |
| Behenyl Alcohol | 0.80 |

| | |
|---|---|
| Isostearyl neopentanoate | 4.50 |
| *Lonicera Caprifolium* (Honeysuckle) Flower Extract (and) *Lonicera Japonica* (Honeysuckle) Flower Extract | 1.00 |
| Powder made in Example 1 | 7.00 |

Process. The Hydroxypropyl Starch Phosphate is mixed with the water then heated to 80 C. The following is added with adequate mixing in between additions; Candelilla/Jojoba/Rice Bran Polyglyceryl-3 Esters (and) Glyceryl Stearate (and) Cetearyl Alcohol (and) Sodium Stearoyl Lactylate, Polyglyceryl-10 Pentastearate (and) Behenyl Alcohol (and) Sodium Stearoyl Lactylate, Glycerin, Cetyl Alcohol, Stearyl Alcohol and Behenyl Alcohol. This mixture is then cooled after homogeneous mixture is obtained. The Isostearyl neopentanoate, *Lonicera Caprifolium* (Honeysuckle) Flower Extract (and) *Lonicera Japonica* (Honeysuckle) Flower Extract and the powder from Example 1 are added with continued mixing.

Example 12

Anti-Wrinkle Cream

| | |
|---|---|
| Water | (Q.S. to) 100 |
| Hydroxypropyl Starch Phosphate | 2.00 |
| Candelilla/Jojoba/Rice Bran Polyglyceryl-3 Esters (and) Glyceryl Stearate (and) Cetearyl Alcohol (and) Sodium Stearoyl Lactylate | 7.00 |
| Polyglyceryl-10 Pentastearate (and) Behenyl Alcohol (and) Sodium Stearoyl Lactylate | 2.00 |
| Glycerin | 5.50 |
| Cetyl Alcohol | 0.80 |
| Stearyl Alcohol | 0.80 |
| Behenyl Alcohol | 0.80 |
| Isostearyl neopentanoate | 4.50 |
| *Lonicera Caprifolium* (Honeysuckle) Flower Extract (and) *Lonicera Japonica* (Honeysuckle) Flower Extract | 1.00 |
| Powder made in Example 2 | 4.00 |

Process. The Hydroxypropyl Starch Phosphate is mixed with the water then heated to 80 C. The following is added with adequate mixing in between additions; Candelilla/Jojoba/Rice Bran Polyglyceryl-3 Esters (and) Glyceryl Stearate (and) Cetearyl Alcohol (and) Sodium Stearoyl Lactylate, Polyglyceryl-10 Pentastearate (and) Behenyl Alcohol (and) Sodium Stearoyl Lactylate, Glycerin, Cetyl Alcohol, Stearyl Alcohol and Behenyl Alcohol. This mixture is then cooled after homogeneous mixture is obtained. The Isostearyl neopentanoate, *Lonicera Caprifolium* (Honeysuckle) Flower Extract (and) *Lonicera Japonica* (Honeysuckle) Flower Extract and the powder from Example 2 are added with continued mixing.

Example 13

Anti-Wrinkle Cream

| | |
|---|---|
| Water | (Q.S. to) 100 |
| Hydroxypropyl Starch Phosphate | 2.00 |
| Candelilla/Jojoba/Rice Bran Polyglyceryl-3 Esters (and) Glyceryl Stearate (and) Cetearyl Alcohol (and) Sodium Stearoyl Lactylate | 7.00 |
| Polyglyceryl-10 Pentastearate (and) Behenyl Alcohol (and) Sodium Stearoyl Lactylate | 2.00 |
| Glycerin | 5.50 |
| Cetyl Alcohol | 0.80 |
| Stearyl Alcohol | 0.80 |
| Behenyl Alcohol | 0.80 |
| Isostearyl neopentanoate | 4.50 |
| *Lonicera Caprifolium* (Honeysuckle) Flower Extract (and) *Lonicera Japonica* (Honeysuckle) Flower Extract | 1.00 |
| Powder made in Example 3 | 3.00 |

Process. The Hydroxypropyl Starch Phosphate is mixed with the water then heated to 80 C. The following is added with adequate mixing in between additions; Candelilla/Jojoba/Rice Bran Polyglyceryl-3 Esters (and) Glyceryl Stearate (and) Cetearyl Alcohol (and) Sodium Stearoyl Lactylate, Polyglyceryl-10 Pentastearate (and) Behenyl Alcohol (and) Sodium Stearoyl Lactylate, Glycerin, Cetyl Alcohol, Stearyl Alcohol and Behenyl Alcohol. This mixture is then cooled after homogeneous mixture is obtained. The Isostearyl neopentanoate, *Lonicera Caprifolium* (Honeysuckle) Flower Extract (and) *Lonicera Japonica* (Honeysuckle) Flower Extract and the powder from Example 3 are added with continued mixing.

Several embodiments have been given that describe possible cosmetic and pharmaceutical uses of the current invention. These embodiments could be modified by someone skilled in the art of cosmetic formulations. It is understood these modifications would not depart from the spirit and scope of the current invention as defined in the appended claims.

Proof of Chemical Identity.

Retinal γ-cyclodextrin hemiacetal, obtained in Example 1, was extracted with the following three solvents; chloroform, iso-propanol, and methanol. The samples for analysis were prepared by accurately weighing 28 mg into a tared vial, next the sample was diluted in 1.0 ml HPLC grade 2-propanol for analysis. After filtering to <1.0 um thru a Teflon syringe filter, the samples were diluted 100 fold with 2-propanol in order to achieve sufficient linearity for analysis. The filtrate was analyzed for retinal. The recovery was found as follows.

| Extraction Solvent | Retinal (%) (Calculated Value 4.5%) |
|---|---|
| Chloroform | 0.04 |
| Iso-propanol | 1.5 |
| Methanol | 4.1 |
| Retinal (control, analyzed directly without extraction step) | 98.0 (Calculated Value 100.0) |

These results clearly establish that retinal is not present as an inclusion complex. Retinal has chemically reacted with γ-cyclodextrin to form retinal γ-cyclodextrin hemiacetal, which chemically reacts with methanol to form retinal in accordance to the following;

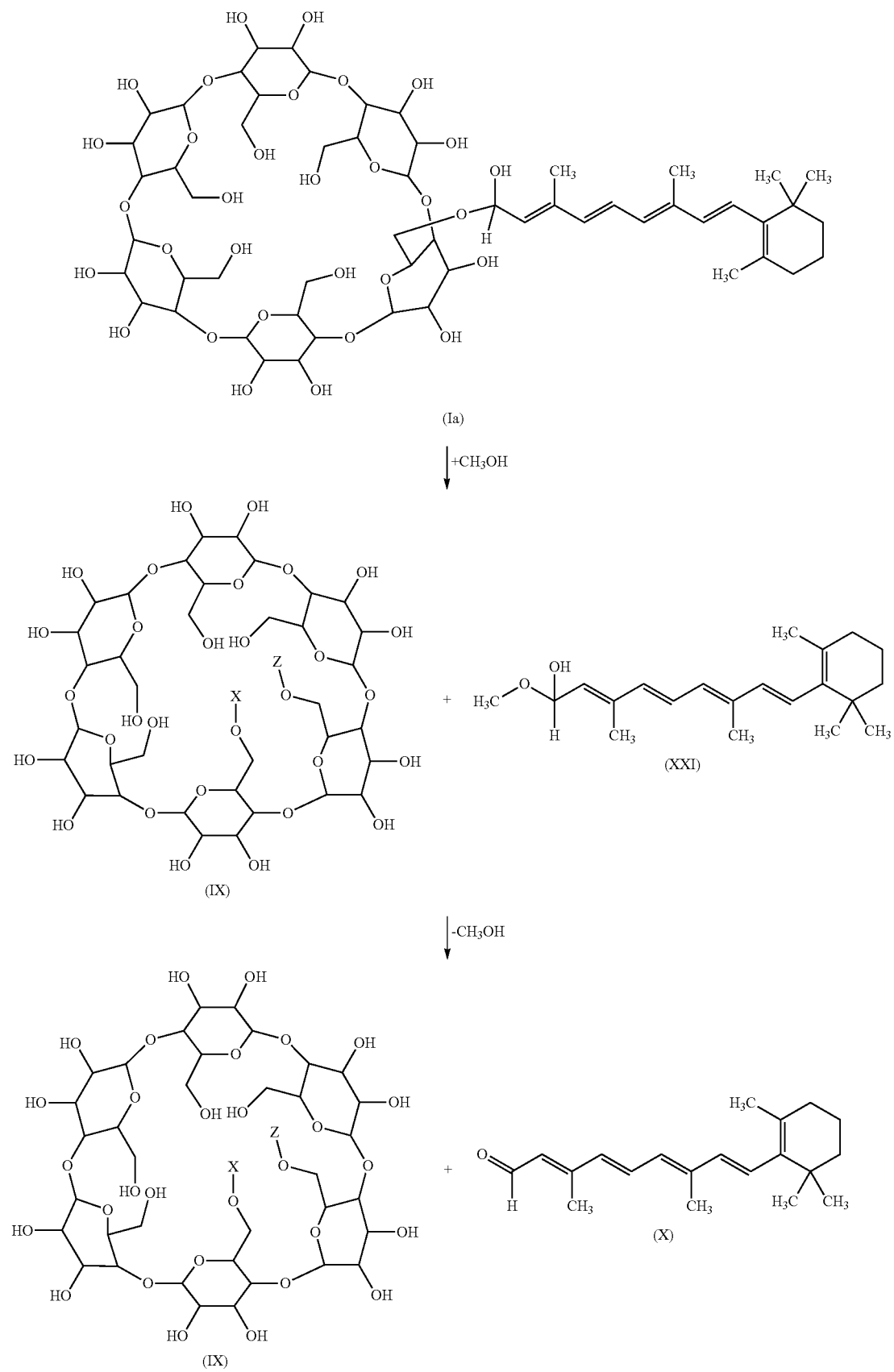

Iso-propanol seems to react very poorly with retinal γ-cyclodextrin hemiacetal.

Skin Complexion Applications.

The compounds of the present invention can release retinal and other aldehydes when exposed to topical acidic pH and moisture of skin. The said property makes these compounds beneficial to treat topical ailments that are treatable by such aldehydes including retinal.

Retinal has been reported to provide the following topical treatment benefits.

Cordero et al. (J Cosmet Dermatol. 2011 June; 10(2):110-7) report retinaldehyde/hyaluronic acid for the management of skin aging, as retinaldehyde was proven effective in treating photo damaged skin.

Merkviladze et al (Georgian Med News. 2010 September; (186):46-50) disclose treatment of noninflammatory acne vulgaris with retinal.

Thielitz et al. (J Dtsch Dermatol Ges. 2010 March; 8 Suppl 1:S15-23) report that topical retinoids are important tools in the management of acne because they act against comedones and microcomedones and have direct anti-inflammatory effects. The substances approved for acne treatment comprise tretinoin (all-trans-retinoic acid), isotretinoin (13-cis retinoic acid) as well as the synthetic third-generation polyaromatic retinoids adapalene and tazarotene, the latter being approved for acne treatment in the US only. Retinaldehyde is used in cosmetic preparations against acne. All topical retinoids are effective as single agents in mild to moderate acne but differ in efficacy and tolerability. Tazarotene 0.1% is more effective than tretinoin 0.025% or 0.1% microsphere gel or adapalene 0.1% gel or cream. Adapalene 0.1% is equally effective to tretinoin 0.025% or tretinoin microsphere 0.1% gel or tretinoin 0.05% cream or isotretinoin 0.05% gel. Adapalene 0.1% gel is significantly better tolerated than tazarotene 0.1% gel, tretinoin 0.025% and tretinoin 0.05% gel, tretinoin 0.05% cream, tretinoin microsphere 0.1% gel or isotretinoin 0.05% gel. The safety profile of topical retinoids differs from their systemic counterparts and is related mainly to local adverse effects, such as erythema, dryness, itching and stinging. The currently available evidence justifies the use of topical retinoids in most types of acne and during maintenance treatment.

Mukherjee et al. (Clin Intery Aging. 2006; 1(4):327-48) report an overview of clinical efficacy and safety of retinoids in the treatment of skin aging. Although retinoids show promise in the treatment of skin aging, irritant reactions such as burning, scaling or dermatitis associated with retinoid therapy limit their acceptance by patients. This problem is more prominent with tretinoin and tazarotene whereas other retinoids mainly represented by retinaldehyde and retinol are considerably less irritating. In order to minimize these side effects, various novel drug delivery systems have been developed. In particular, nanoparticles have shown a good potential in improving the stability, tolerability and efficacy of retinoids like tretinoin and retinol.

Stefanaki et al. (J Cosmet Dermatol. 2005 June; 4(2):130-4) report topical retinoids in the treatment of photoaging. A large number of different substances comprise the family of retinoids, which are traditionally described as vitamin A derivatives. By exerting their action through nuclear and cytoplasmic receptors they may improve photoaging. Tretinoin is the best studied retinoid in the treatment of photoaging. Others such as isotretinoin, retinaldehyde, and tazarotene, although less well studied, have given promising results.

Sorg et al. (Dermatol Ther. 2006 September-October; 19(5):289-96) report the benefits of retinoids in cosmeceuticals. Retinoids are natural and synthetic vitamin A derivatives. They are lipophilic molecules and easily penetrate the epidermis. Their biologically active forms can modulate the expression of genes involved in cellular differentiation and proliferation. Retinoic acid (tretinoin), its 13-cis isomer isotretinoin, as well as various synthetic retinoids are used for therapeutic purposes, whereas retinaldehyde, retinol, and retinyl esters, because of their controlled conversion to retinoic acid or their direct receptor-independent biologic action, can be used as cosmeceuticals. These natural retinoic acid precursors are thus expected to be helpful in (i) renewing epidermal cells, (ii) acting as UV filters, (iii) preventing oxidative stress, (iv) controlling cutaneous bacterial flora, and (v) improving skin aging and photoaging. Retinol and retinyl esters are not irritant, whereas demonstrating only a modest clinical efficiency. On the other hand, retinaldehyde, which is fairly well tolerated, seems to be the most efficient cosmeceutical retinoid; it has significant efficiency toward oxidative stress, cutaneous bacterial flora, epidermis renewing, and photoaging.

Ortonne (Dermatol Ther. 2006 September-October; 19(5): 280-8) reports retinoid therapy of pigmentary disorders. Topical retinoids such as all-trans-retinoic acid (RA), 13-cis-retinoic acid (isotretinoin), retinol, retinaldehyde, tazarotene, and adapalene have been shown to improve dyspigmentation of photodamaged skin including mottling and actinic lentigines. RA monotherapy has also been demonstrated to improve melasma and postinflammatory hypermelanosis. Furthermore, RA in combination with hydroquinone or 4-hydroxyanisole, or azelaic acid increases the potency of depigmenting agents for the treatment of melasma, actinic lentigines, and postinflammatory hypermelanosis. The basic mechanisms underlying these effects are not completely identified. Topical retinoids stimulate the cell turn-over of epidermal keratinocytes and promote a decrease in melanosome transfer and a rapid loss of melanins via epidermopoiesis. Topical retinoids are also involved in the control of cell differentiation. Retinoid-induced changes in the stratum corneum and the permeability barrier may also facilitate the penetration of depigmenting agents in the epidermis and increase their bioavailability, leading to increased depigmentation. In addition, several in vitro studies demonstrate that cis and trans-retinoic acid inhibit UV-B stimulated melanogenesis in term of tyrosinase activity and melanin synthesis. It is likely that topical retinoids modulate epidermal melanin count via a direct action on melanocytes and epidermal keratinocytes.

Stratigos et al. (Drugs. 2005; 65(8):1061-72) report the role of topical retinoids in the treatment of photoaging. Aging of the skin is a complex biological process which is influenced by the interaction of several intrinsic and extrinsic factors. Intrinsic or chronological aging is an inevitable, genetically programmed process, of unclear underlying mechanism, for which no prevention or effective treatment is currently available. Photoaging refers to the gross and microscopic cutaneous changes that are induced by cumulative exposure to UV radiation and are superimposed on the background of chronological aging. Although primarily an aesthetic problem with significant psychological effects, photoaging constitutes the background for the development of precancerous and cancerous skin lesions. Overwhelming clinical and histological evidence indicate that certain structural changes induced by excessive sun exposure can be reversed, to some extent, by the use of topical retinoids. A number of retinoid compounds, for example tretinoin, isotretinoin, retinaldehyde and tazarotene, have been employed for the treatment of photoaged skin, and demonstrate beneficial clinical and histological effects.

Sorg et al. (Photochem Photobiol. 2005 July-August; 81(4):830-6) report topical retinoids prevent DNA damage and apoptosis after acute UV-B exposure in hairless mice.

Kasraee et al. (Dermatology. 2005; 210 Suppl 1:30-4) report the depigmenting effect of RALGA, a combination of the less irritant retinoid retinaldehyde and glycolic acid. It has been known for a long time that the topical use of retinoic acid (RA) produces mild depigmentation of human skin. However, RA has two major disadvantages for its utilization as a topical depigmenting compound. First, RA can act as an irritant and can produce considerable erythema and exfoliation of skin. Second, RA has a relatively weak depigmenting ability compared to other known depigmenting chemicals. RALGA, a combination of the less irritant retinoid retinaldehyde (RAL; 0.1%) and glycolic acid (6.4%), has a higher skin-depigmenting potential than RA 0.05% in the tail skin of C57BL/6 mice. This effect was observed in reducing the number of functioning melanocytes and/or in inhibiting their ability to synthesize melanin. In addition, the visually recognizable depigmenting effect of RALGA was evident earlier than that of RA, i.e. only after 1 week of application. RALGA may therefore serve as a depigmenting product for the treatment of skin hyperpigmentary disorders. Post acne hyperpigmented lesions represent a very common pigmentary problem among acne patients. RALGA may thus act as an anti-acne product, due to the presence of RAL, an RA precursor, which could simultaneously remove the post acne hyperpigmented lesions in such patients.

Dreno et al. (Dermatology. 2005; 210 Suppl 1:22-9) report results of topical retinaldehyde with glycolic acid in a study of tolerance and acceptability in association with anti-acne treatments in 1,709 patients. The data show that a combination of RAL 0.1% and glycolic acid 6% may be used in association with other topical anti-acne treatments (benzoyl peroxide and topical antibiotics) with an excellent tolerance.

Pechere et al (Dermatology. 2002; 205(2):153-8) report the antibacterial activity of topical retinoids and retinaldehyde. Of the three retinoids tested, only RAL showed a significant in vitro antibacterial activity; this activity was found against reference strains of gram-positive bacteria like *S. aeureus, Micrococcus* spp. or *P. acnes*.

Vienne et al. (Dermatology. 1999; 199 Suppl 1:53-6) report that retinaldehyde has beneficial effects on the vascular component of facial rosacea.

Creidi et al. (Dermatology. 1999; 199 Suppl 1:49-52) report that retinaldehyde is efficient and well tolerated for the improvement of the signs of photoaging via controlled clinical studies using image analysis of silicone skin replicas.

Boisnic et al. (Dermatology. 1999; 199 Suppl 1:43-8) report the repair of UVA-induced elastic fiber and collagen damage by 0.05% retinaldehyde cream in an ex vivo human skin model. It has been shown that retinaldehyde has many of the properties of tretinoin in its biological and beneficial effects on photoaging. These authors have verified some of these previous observations, especially on dermal connective tissue, by obtaining significant repair of elastic fibers and collagen alteration induced by UVA exposure.

Pechere et al. (Dermatology. 1999; 199 Suppl 1:29-31) report the effect of retinaldehyde on *Propionibacterium acnes*, both in vivo and in vitro. The MIC of retinaldehyde against *P. acnes* suggests a direct antibacterial activity. Daily topical application of 0.05% retinaldehyde is associated with a clear reduction of the *P. acnes* density.

The above prior art clearly establishes topical benefits of retinal: management of skin aging, treatment of skin aging, treating photo damaged skin, treatment of noninflammatory acne vulgaris, anti-inflammatory effects, treatment of photoaging, renewing epidermal cells, acting as UV filters, preventing oxidative stress, controlling cutaneous bacterial flora, improving skin aging and photoaging, therapy of skin pigmentation disorders, preventing DNA damage, skin depigmenting effect, anti-acne treatments, antibacterial activity, facial rosacea, and repair of UVA-induced elastic fiber and collagen damage. Since topical photo damage is known to be responsible for dark skin coloration, wrinkles, and fine lines all retinal treatments also treat these skin complexion problems as well. As the compounds of the present invention can deliver retinal upon topical application, due to the chemical reaction with topical acidic pH and moisture, all of the above referenced treatment benefits of retinal are also applicable to be compounds of the present invention.

Stability.

The compounds of the present invention, especially hemiacetals, possess both unexpected and surprising stability. It is postulated that this property may be due to hydrogen bonding of —OH group of said hemiacetal with primary hydroxyl groups of cyclodextrin moiety of these molecules in accordance to example in formula (XXII);

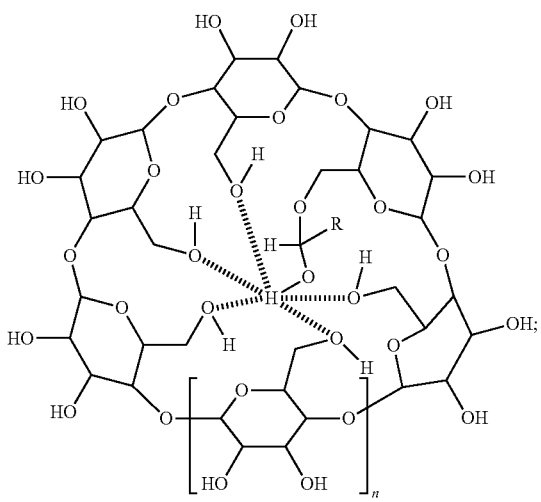

(XXII)

wherein,
n=3.

However, the actual reason for this stability of formula (XXII) may still be unknown. However, this does not impact the skin care treatment benefits of the compounds of the present invention.

The invention claimed is:

1. A compound of formula (I), or an isomer thereof;

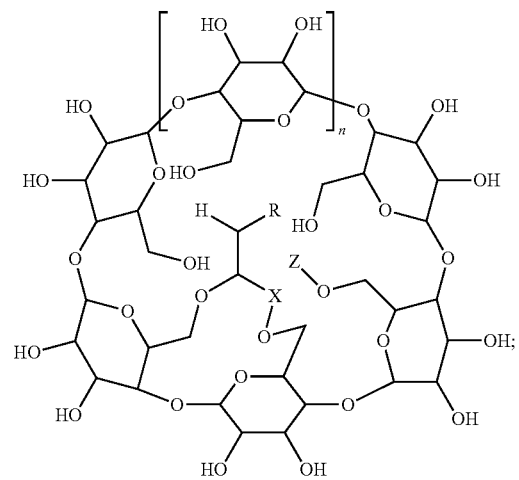

(I)

wherein,
n=0 to 4, and
X=a direct bond, —CH$_2$—CH$_2$—O—, or —CH$_2$—CH$_2$—CH$_2$—O—, and
Z=H, —CH$_2$—CH$_2$—OH, —CH$_2$—CH$_2$—CH$_2$—OH, —SO$_3$H, —SO$_3$M, —PO$_3$H$_2$, —PO$_3$M, or —PO$_3$M$_2$, and
R=a retinoid, or a carotenoid, and
M=Na, K, Ca, Mg, Ba, Zn, Mn, Cu, Fe, Co, or Ni.

2. The compound of claim 1, wherein n is 1, 2, or 3, and X is a direct bond.

3. The compound of claim 1, wherein R is selected from the group consisting of:

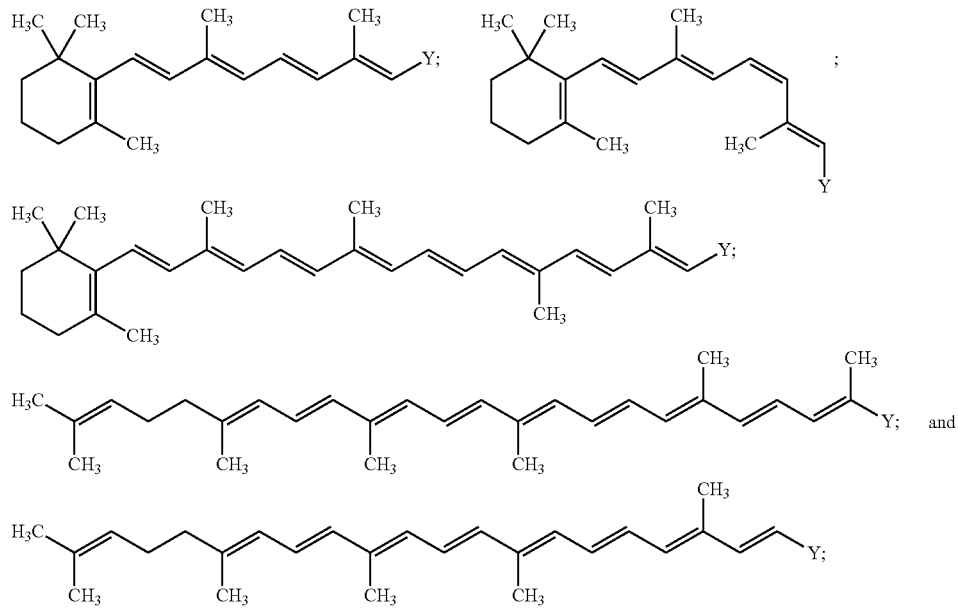

wherein,
Y=point of attachment.

4. The compound of claim 1, wherein said compound is of formula (II);

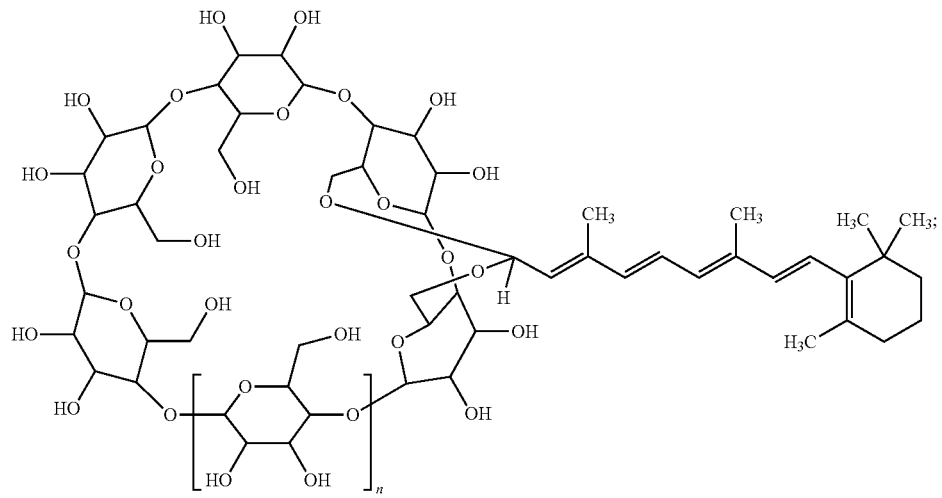

wherein,
n=3.

5. A composition comprising a compound of claim 1.

6. A composition comprising a compound of claim 1, wherein said composition treats an ailment related to skin complexion.

7. A composition comprising a compound of claim 1, wherein said composition comprises a pharmaceutical, nutraceutical, or cosmetic composition.

8. The composition of claim 7, wherein said composition further comprises *Lonicera caprifolium* flower extract, or *Lonicera japonica* flower extract, or combinations thereof.

9. A composition comprising a compound of claim 1, wherein said composition further comprises water, emulsifying wax, ensulizol, octinoxate, propyleene glycol, gluconolactone, sodium benzoate, triethanolamine, ammolnium acryloyldimethyltaurate/VP copolymer, titanium dioxide, and combinations thereof.

10. A composition comprising a compound of claim 1, wherein said composition further comprises water, hydroxypropyl starch phosphate, candelilla wax, jojoba wax, rice bran polyglyceryl esters, glyceryl stearate, cetearyl alcohol, sodium stearoyl lactate, polyglyceryl-10 pentastearate, behenyl alcohol, glycerin, cetyl alcohol, stearyl alcohol, isostearyl neopentanoate, *Lonicera caprifolium* flower extract, *Lonicera japonica* flower extract, and combinations thereof.

11. A composition comprising a compound of claim 1, wherein said composition further comprises water, carbopol, *Lonicera caprifolium* flower extract, *Lonicera japonica* flower extract, and combinations thereof.

12. A method of treating, reducing the occurrence of, or improving the symptoms associated with a condition selected from the group consisting of: acne and skin darkening; age spots; loss of cellular antioxidants; skin changes associated with aging including collagen loss; loss of skin pliability; loss of skin suppleness; skin wrinkles and fine lines; damage from radiation and damage from free radicals; dry skin; xerosis; ichthyosis; dandruff; keratoses; melasma; lentigines; liver spots; skin pigmentation; pigmented spots, dark circles under the eyes, darkened skin, and blemishes; oily skin; warts; eczema; pruritic skin; psoriasis; inflammatory dermatoses; topical inflammation; scalp dryness and combinations thereof; which comprises administering the compound of claim 1 to a subject in need thereof.

13. The composition of claim 5, wherein said composition comprises a topically administrable or orally administrable composition.

14. The method of claim 12, wherein the condition is acne and skin darkening.

15. The method of claim 12, wherein the condition is skin wrinkles and fine lines.

16. A process for making a compound of claim 1, wherein said process comprises (i) first mixing a polyene aldehyde and an organic solubilizing liquid until a transparent mixture is obtained; (ii) to this mixture a suitable cyclodextrin and water are added and mixed for 1-120 hours under a nitrogen or argon atmosphere; (iii) the reaction mixture is then dried to a powder; (iv) the preferred method of drying is spray drying.

* * * * *